(12) United States Patent
Harrison

(10) Patent No.: US 11,478,592 B2
(45) Date of Patent: Oct. 25, 2022

(54) DEVICE FOR MEDICAL BREATHING TREATMENT

(71) Applicant: Johnathan Harrison, Henryetta, OK (US)

(72) Inventor: Johnathan Harrison, Henryetta, OK (US)

(73) Assignee: Loli-O's, LLC, Spring Hill, TN (US)

( * ) Notice: Subject to any disclaimer, the term of this patent is extended or adjusted under 35 U.S.C. 154(b) by 646 days.

(21) Appl. No.: 16/158,871

(22) Filed: Oct. 12, 2018

(65) Prior Publication Data

US 2019/0111223 A1 Apr. 18, 2019

Related U.S. Application Data

(60) Provisional application No. 62/571,325, filed on Oct. 12, 2017.

(51) Int. Cl.
*A61M 15/00* (2006.01)
*A61M 16/14* (2006.01)
(Continued)

(52) U.S. Cl.
CPC ......... *A61M 15/0086* (2013.01); *A23G 3/563* (2013.01); *A61M 11/06* (2013.01); *A61M 15/0021* (2014.02); *A61M 15/08* (2013.01); *A61M 16/0003* (2014.02); *A61M 16/12* (2013.01); *A61M 16/14* (2013.01);
(Continued)

(58) Field of Classification Search
CPC .............. A61M 15/0086; A61M 16/14; A61M 16/0003; A61M 2202/0208; A61M 2205/59; A61M 11/06; A61M 15/0021; A61M 15/08; A61M 16/12; A61M 11/002; A61M 15/0043; A61M 2021/0016;
(Continued)

(56) References Cited

U.S. PATENT DOCUMENTS 4,192,307 A * 3/1980 Baer ..................... A23G 3/34
606/236
4,746,067 A * 5/1988 Svoboda ............... A61M 11/06
239/338
(Continued)

OTHER PUBLICATIONS

Loli-O's facebook page, video dated Aug. 6, 2016; https://www.facebook.com/loliosnebulizer/.

*Primary Examiner* — Victoria Murphy
(74) *Attorney, Agent, or Firm* — Waller Lansden Dortch & Davis, LLP; Blake M. Bernard

(57) ABSTRACT

A breathing treatment delivery device is disclosed for providing atomized medicine or oxygen to a patient. The breathing treatment delivery device can include a supply device configured to dispense atomized medicine or oxygen through a dispensing end of the supply device. A cap can have a device side and a delivery side, the device side including an opening receiving and in fluid communication with the dispensing end of the supply device. A treat holder can be positioned on the delivery side of the cap. At least one aperture can be defined in the delivery side of the cap adjacent the treat holder, a pneumatic passage formed through the cap between the opening in the device side of the cap and the aperture. A patient can enjoy a piece of candy or other treat retained by the treat holder during treatment while breathing in the desired medicine or oxygen.

13 Claims, 11 Drawing Sheets

(51) Int. Cl.
*A61M 16/12* (2006.01)
*A61M 16/00* (2006.01)
*A61M 11/06* (2006.01)
*A23G 3/56* (2006.01)
*A61M 15/08* (2006.01)
*A61J 7/00* (2006.01)
*A61M 11/00* (2006.01)
*A61M 21/00* (2006.01)

(52) U.S. Cl.
CPC ............. *A61J 7/003* (2013.01); *A61M 11/002* (2014.02); *A61M 15/0043* (2014.02); *A61M 2021/0016* (2013.01); *A61M 2202/0208* (2013.01); *A61M 2205/588* (2013.01); *A61M 2205/59* (2013.01); *A61M 2210/0618* (2013.01); *A61M 2210/0625* (2013.01)

(58) Field of Classification Search
CPC .... A61M 2205/588; A61M 2210/0618; A61M 2210/0625; A23G 3/563; A61J 7/003
See application file for complete search history.

(56) References Cited

U.S. PATENT DOCUMENTS

| | | | |
|---|---|---|---|
| 5,904,140 A | 5/1999 | McGoogan | |
| 6,526,966 B1* | 3/2003 | Peesay | A61J 9/00 128/200.14 |
| 6,626,168 B1* | 9/2003 | Carroll | A61M 16/06 128/200.14 |
| 7,318,433 B2* | 1/2008 | Cockerham | A61M 16/10 128/201.26 |
| 2003/0205234 A1* | 11/2003 | Bardach | A63B 71/085 128/861 |
| 2005/0188992 A1 | 9/2005 | Cockerham | |
| 2006/0240381 A1* | 10/2006 | Rizoiu | A61C 1/0046 433/80 |
| 2009/0062855 A1 | 3/2009 | Lemery et al. | |
| 2012/0186582 A1 | 7/2012 | Addington et al. | |

* cited by examiner

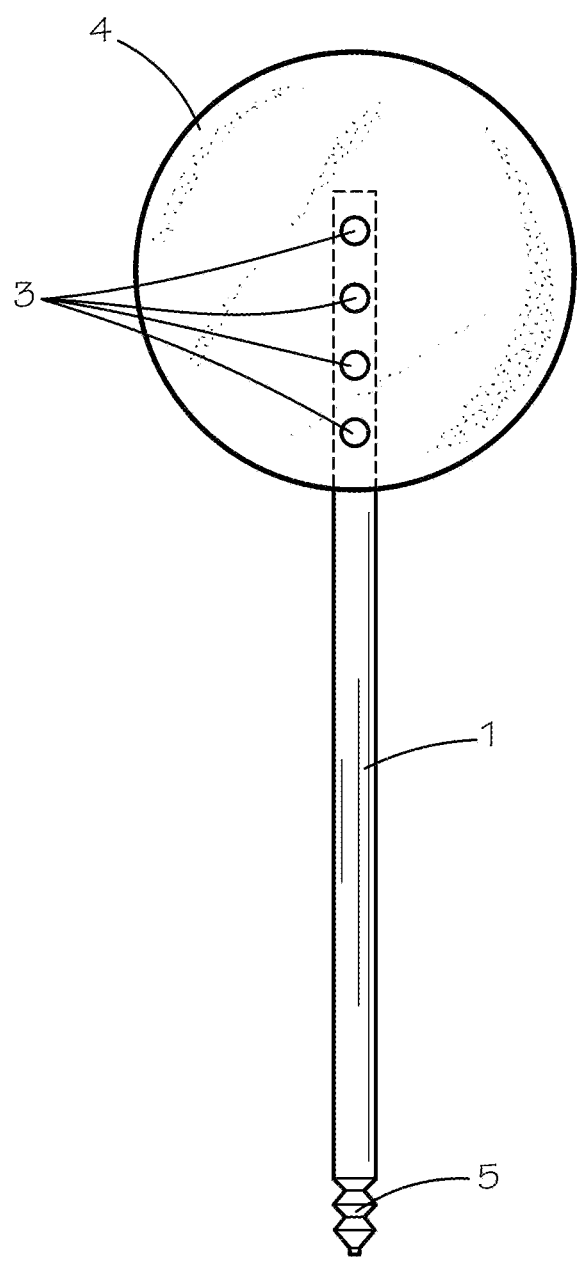
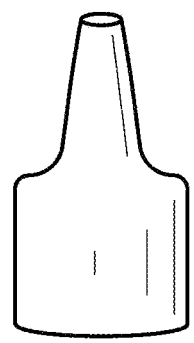
FIG. 1                FIG. 2

DEVICE FOR MEDICAL BREATHING TREATMENT

CROSS-REFERENCES TO RELATED APPLICATIONS

This application is a non-provisional of U.S. Patent Application No. 62/571,325 filed Oct. 12, 2017 entitled DEVICE FOR MEDICAL BREATHING TREATMENT, which is hereby incorporated by reference in its entireties.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to medical breathing treatment devices such as oxygen breathing treatment devices and medical nebulizer devices which can deliver oxygen or medication in atomized, aerosol, or mist form as a breathing treatment, the patient breathing in the oxygen or atomized spray during treatment. Such treatments are known to be effective in treating a variety of medical conditions including but not limited to asthma and other respiratory conditions.

More particularly, the present disclosure relates to breathing treatment devices including medical nebulizer devices for patients who are intimidated or panicked by medical breathing treatments including but not limited to children or younger patients. Conventional breathing treatment devices can be connected to a mask worn by the patient, the patient breathing in the atomized spray or mist from the mask directly into the lungs. In other embodiments, a mouthpiece can be connected to the nebulizer, the atomized spray being delivered via the mouthpiece during treatment. A patient would insert the mouthpiece into their mouth and breathe in the treatment directly into the patient's lungs.

Such conventional methods can be sufficient for some patients. However, many younger patients such as children, as well as adult patients who become anxious or panicked by breathing treatments, can be intimidated by a mask that is placed on their face or a mouthpiece inserted into their mouth. Such patients can resist treatment, and often remove the mask or the mouthpiece during treatment. Removal of the delivery device for the atomized medication from the patient's face or mouth can decrease the efficiency and effectiveness of the treatment as medication or oxygen is wasted and not delivered to the patient if the delivery device is removed from the patient's face and mouth.

What is needed then are improvements to medical nebulizer devices.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the present disclosure is a breathing treatment delivery device for providing atomized medicine or oxygen to a patient. The breathing treatment delivery device can include a supply device configured to dispense atomized medicine or oxygen through a dispensing end of the supply device. A cap can have a device side and a delivery side, the device side including an opening receiving and in fluid communication with the dispensing end of the supply device. A treat holder can be positioned on the delivery side of the cap. At least one aperture can be defined in the delivery side of the cap adjacent the treat holder, a pneumatic passage formed through the cap between the opening in the device side of the cap and the aperture.

During treatment, a patient can place a candy, edible item, or other treat in the treat holder and place the item into the patient's mouth. As the patient sucks on or eats the candy, the patient will breathe in the atomized medicine or oxygen treatment to deliver the medicine or oxygen to the patient's lungs. The candy or treat can provide a distraction to the patient, which helps remove the intimidating environment associated with conventional masks and mouthpiece devices. The candy can help effectively distract the patient while the breathing treatment is properly delivered.

Another aspect of the present disclosure is a cap for a breathing treatment device having a breathing device side and a delivery side, the breathing device side receivable on the breathing treatment device. The cap can include a candy holder that includes a candy holder recess open to the delivery side of the cap in some embodiments. At least one aperture is defined on the delivery side of the cap, the aperture fluidly communicating the breathing device side of the cap with the delivery side of the cap.

The cap can be utilized to provide a patient, such as a child, with a treat, candy or other edible item such as a sucker, lollipop, etc., to suck on and eat during treatment. The presence of the candy on the cap of the nebulizer can provide a distraction and/or reward to the patient, which can make the treatment less intimidating and can encourage proper administration of the breathing treatment to the patient. During treatment, a patient can place the candy in the patient's mouth such that the patient's nose and mouth are positioned proximate to the one or more apertures in the cap where the atomized spray is emitted. As such, an effective pass by or blow by treatment of atomized medicine can be delivered to the patient as the patient is sucking on and distracted by the candy on the cap of the nebulizer.

Another aspect of the present disclosure is a breathing treatment device for delivery of a medicine to a patient, the device including a nebulizer having a pneumatic end, a dispensing end, and a medicine reservoir positioned between the pneumatic end and the dispensing end, the medicine receivable in the medicine reservoir. The nebulizer can be configured to receive pressurized gas through the pneumatic end of the nebulizer, the pressurized gas atomizing the medicine contained in the medicine reservoir to emit an atomized medicine spray through the dispensing end of the nebulizer. A cap can be disposed on the dispensing end of the nebulizer, the cap including a nebulizer side and a delivery side, the nebulizer side disposed on the dispensing end of the nebulizer. A treat holder can be disposed on the delivery side of the cap, the candy holder including a treat holder recess in some embodiments. At least one aperture is defined in the base, the aperture fluidly communicating the nebulizer side of the cap with the delivery side of the cap to emit the atomized spray from the nebulizer through the at least one aperture.

Numerous other objects, advantages and features of the present disclosure will be readily apparent to those of skill in the art upon a review of the following drawings and description of a preferred embodiment.

BRIEF DESCRIPTION OF THE DRAWINGS

FIG. 1 is a front elevation view of an embodiment of a breathing treatment delivery device of the present disclosure.

FIG. 2 is a front elevation view of a connection member for connecting the breathing treatment delivery device of FIG. 1 to pneumatic tubing or hoses.

DETAILED DESCRIPTION

Figure 3:
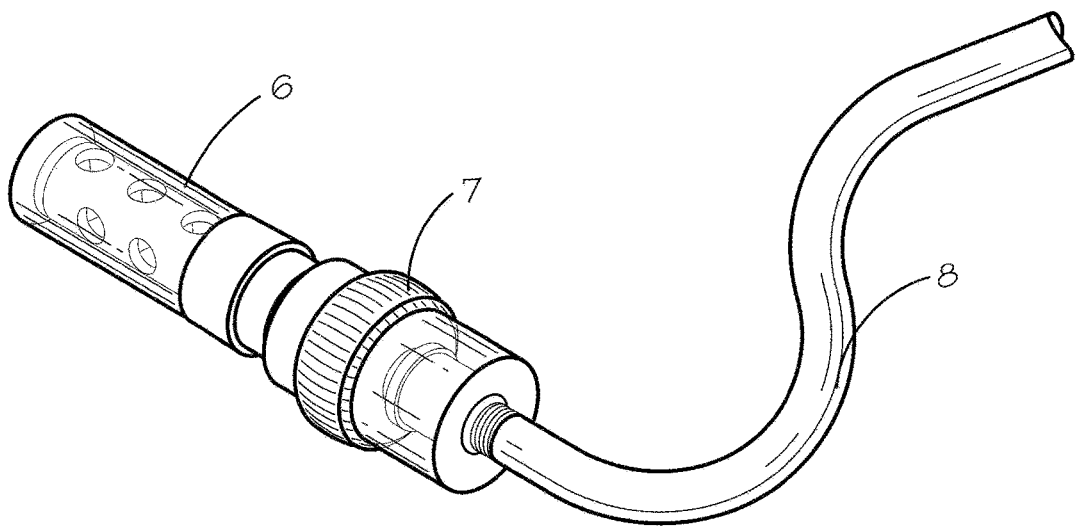
FIG. 3 is a perspective view of another embodiment of a breathing treatment delivery device of the present disclosure.

Various aspects of the illustrative embodiments will be described using the terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

In one embodiment of the present disclosure, a device that can deliver up to several liters of oxygen per minute as well as deliver nebulized breathing medications, including but not limited to albuterol or other respiratory medications, via a standard nebulizer is disclosed.

The devices of the present disclosure may be considered a "delivery" device, and varying dosages of any particular medication. The devices of the present disclosure can deliver a desired dosage for a breathing medication and/or oxygen that is ordered by a physician and can be used for patients such as children who panic at the sight of medicine being delivered through a mask or mouth piece delivery device directly.

In some embodiments, the delivery device can allow for self-administration of the medication and/or oxygen by a child, while the child is enjoying an edible item such as a candy, sucker or lollipop positioned on the device. Many physicians order what is called "blow-by" oxygen and breathing medications, which simply means that the oxygen or medication is to be passed or blown within a very close proximity of the child's face. With the devices of the present disclosure, this is achieved very easily by having the patient lick or suck on the candy or lollipop to maintain the device near the face of the patient as atomized medicine spray or oxygen is delivered via the delivery device. In some embodiments, the delivery of oxygen or medication is not predicated on the candy or lollipop being licked or positioned in the patient's mouth.

In some embodiments, each device can be designed for single patient use only. Once the breathing medication or oxygen has been delivered as ordered, the delivery device can be discarded into the trash or otherwise disposed of. In other embodiments, the device can be cleanable and reusable with a new candy or edible item swapped out between uses. The device can include an edible item or candy such as a sucker, lollipop, or other item can require a considerable amount of time to eat or dissolve. As such, the patient will be encouraged to eat or suck on the candy or other edible item for an extended period of time to help ensure a proper dosage or amount of medication and/or oxygen is delivered during the breathing treatment. The candy can be manufactured in a variety of flavors, shapes, sizes, etc.

Figure 4:
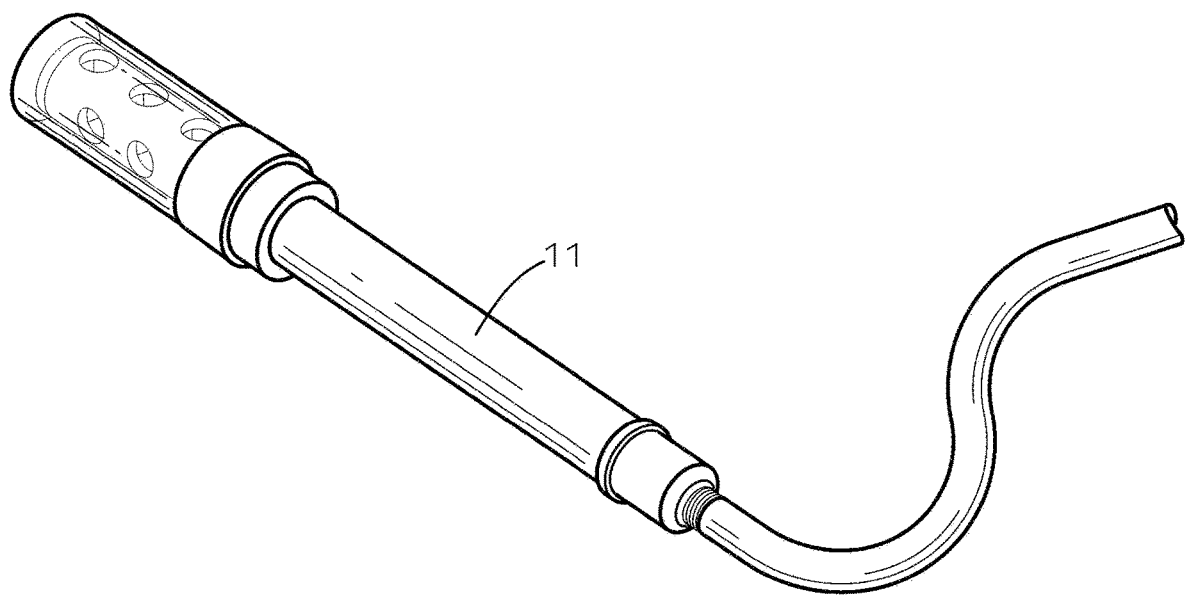
FIG. 4 is a perspective view of another embodiment of a breathing treatment delivery device of the present disclosure.

One embodiment of a breathing device is shown in FIGS. 1-2. In some embodiments, the device can include a hollow base 1 that will accept a standard nebulizer, or a pneumatic tubing connected to and extending from a nebulizer device or a pneumatic supply such as an oxygen supply. The hollow base 1 can have a pneumatic end 5 and a distal end opposite the pneumatic end 5. The pneumatic end 5 can be connected to a nebulizer device, an oxygen supply, or pneumatic tubing. An edible substance such as candy material 4 can be poured and formed around a distal end of the hollow base 1. Base apertures 3 can be drilled into the distal end of the base 1. Candy apertures can also be drilled through the candy and aligned with the base apertures 3 in the distal end of the hollow base 1. As such, atomized medicine spray or oxygen can pass into the pneumatic end 5 of the hollow base 1, through the hollow base 1, and out of the base apertures 3 and the candy apertures to emit the oxygen and/or atomized medicine from the device. The base apertures 3 and candy apertures can be positioned at various orientations. In some embodiments, as shown in FIGS. 3-4, the candy apertures and base apertures can be spaced radially about the distal end of the base and the candy such that oxygen and/or atomized medicine can be emitted generally from all sides of the device.

The hollow base 1 and the candy 4 can generally form various candy, sucker, or lollipop shapes, as shown in FIGS. 1-4, such that the device looks and feels like a conventional candy, sucker, or lollipop to a younger patient such as a child, which can help remove anxiety associated with the treatment.

FIG. 1 shows the base 1 and candy 4 in the shape of a lollipop having a circular candy 4 and the base 1 having the shape of a plastic stick. In some embodiments, the candy material 4 used can be a sugar free edible substance available in various flavors and varied shapes. The pneumatic end 5 of the hollow stick 1 is designed to accept oxygen or other pneumatic tubing. Having the base 1 connected to tubing can also allow the pumps, compressors, nebulizers, or other intimidating equipment to be positioned remotely from the patient, which can further help decrease the anxiety of the patient associated with the treatment.

FIG. 2 is a front perspective view of an embodiment of an adapter for a standard nebulizer. The adapter can be positioned on a nebulizer and connected either directly to the hollow base or to pneumatic tubing which can supply atomized medicine from the nebulizer to the hollow base.

FIG. 3 is a perspective view of another embodiment of the device wherein the base includes a nebulizer assembly 7. As such, pressurized gas can be delivered to the base and into the nebulizer 7 via pneumatic tubing 8 and atomized medicine can be delivered from the nebulizer 7, through the base, and out the candy 6. The nebulizer 7 can be configured to atomize liquid medicine disposed in the nebulizer 7 via the pressurize gas or air supplied to the nebulizer.

FIG. 4 is a perspective view of another embodiment of a delivery device assembled, with the base 11 connected to pneumatic tubing which can be connected to a nebulizer or an oxygen supply.

Figure 5:
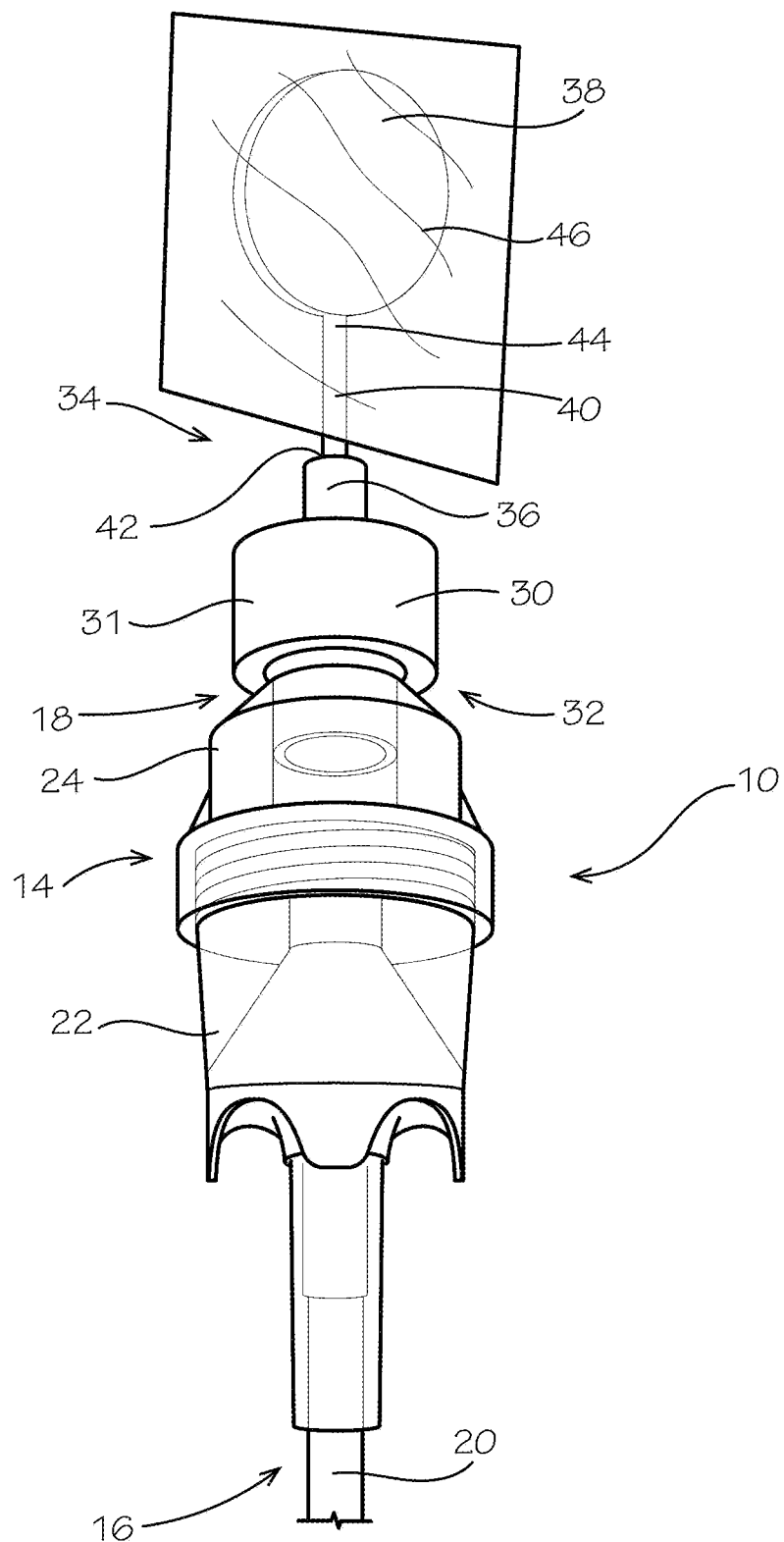
FIG. 5 is a front perspective view of another embodiment of a breathing treatment delivery device of the present disclosure including a cap with a candy holder.
Figure 6:
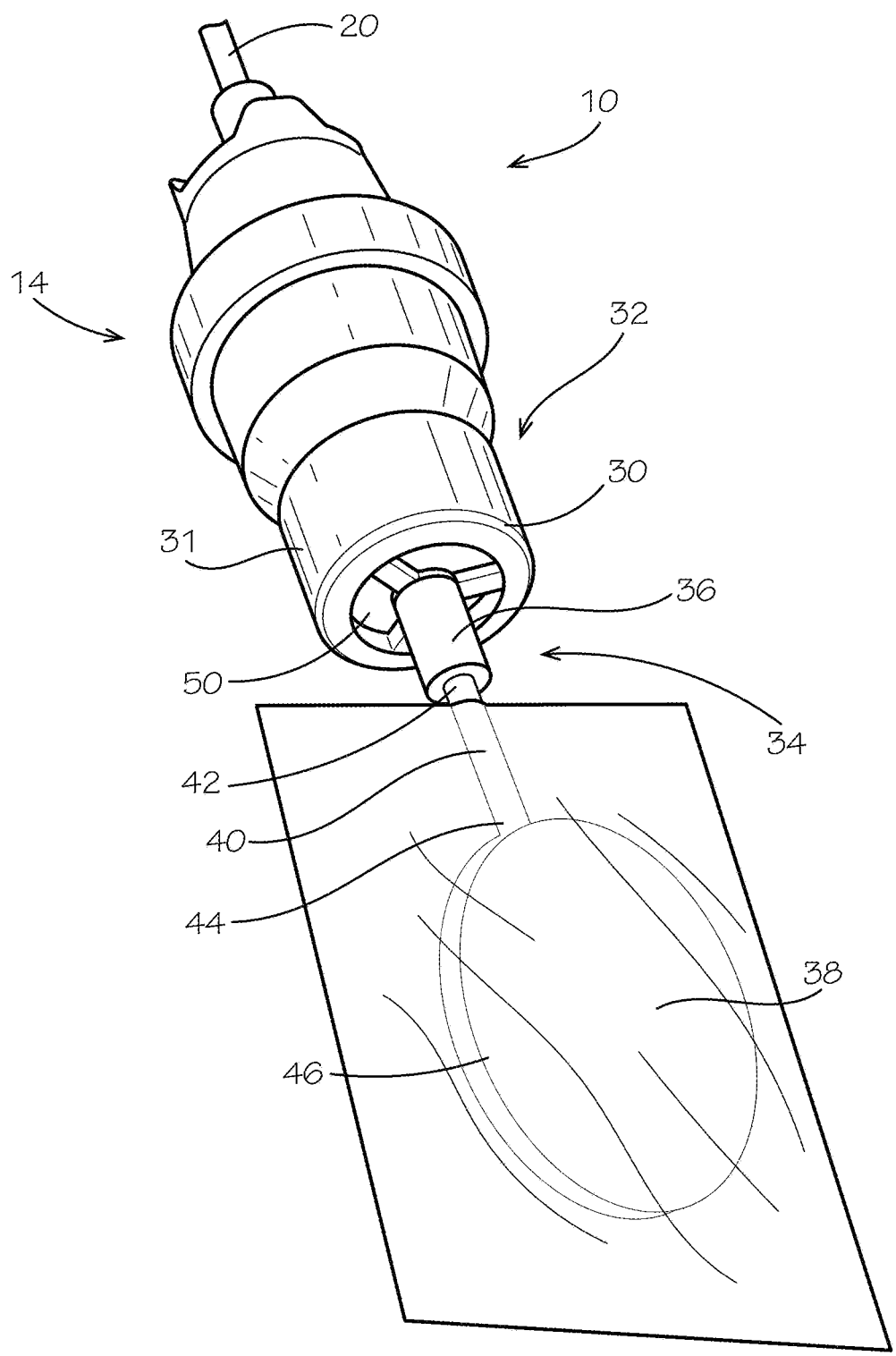
FIG. 6 is a top perspective view of the device of FIG. 5.

Another embodiment of a breathing treatment delivery device 10 is shown in FIGS. 5-13. One aspect of the present disclosure is a cap 30 for a breathing treatment delivery device 10 which can include a supply device 14 such as a nebulizer or an oxygen delivery device. The cap 30 can include a device side 32 and a delivery side 34. The device side 32 can be receivable on the breathing treatment delivery device 14. The device side 32 can also be described as a nebulizer side when the breathing treatment delivery device 14 is a nebulizer, as shown in FIG. 5. In some embodiments, the breathing device side 32 of the cap 30 can be sized and shaped to produce an interference fit or friction fit with a dispensing end 18 of the supply device 14 when the cap 30 is positioned on the supply device 14 in order to retain the cap 30 on the supply device 14. In other embodiments, the cap 30 can threadingly engage the supply device 14. In still other embodiments, the dispensing end 18 of a supply device 14 can include pneumatic tubing, and the cap 30 can be sized to be received on the pneumatic tubing. In some embodiments, the cap 30 can produce an interference or friction fit with any pneumatic tubing extending from the supply device 14.

Figure 7:
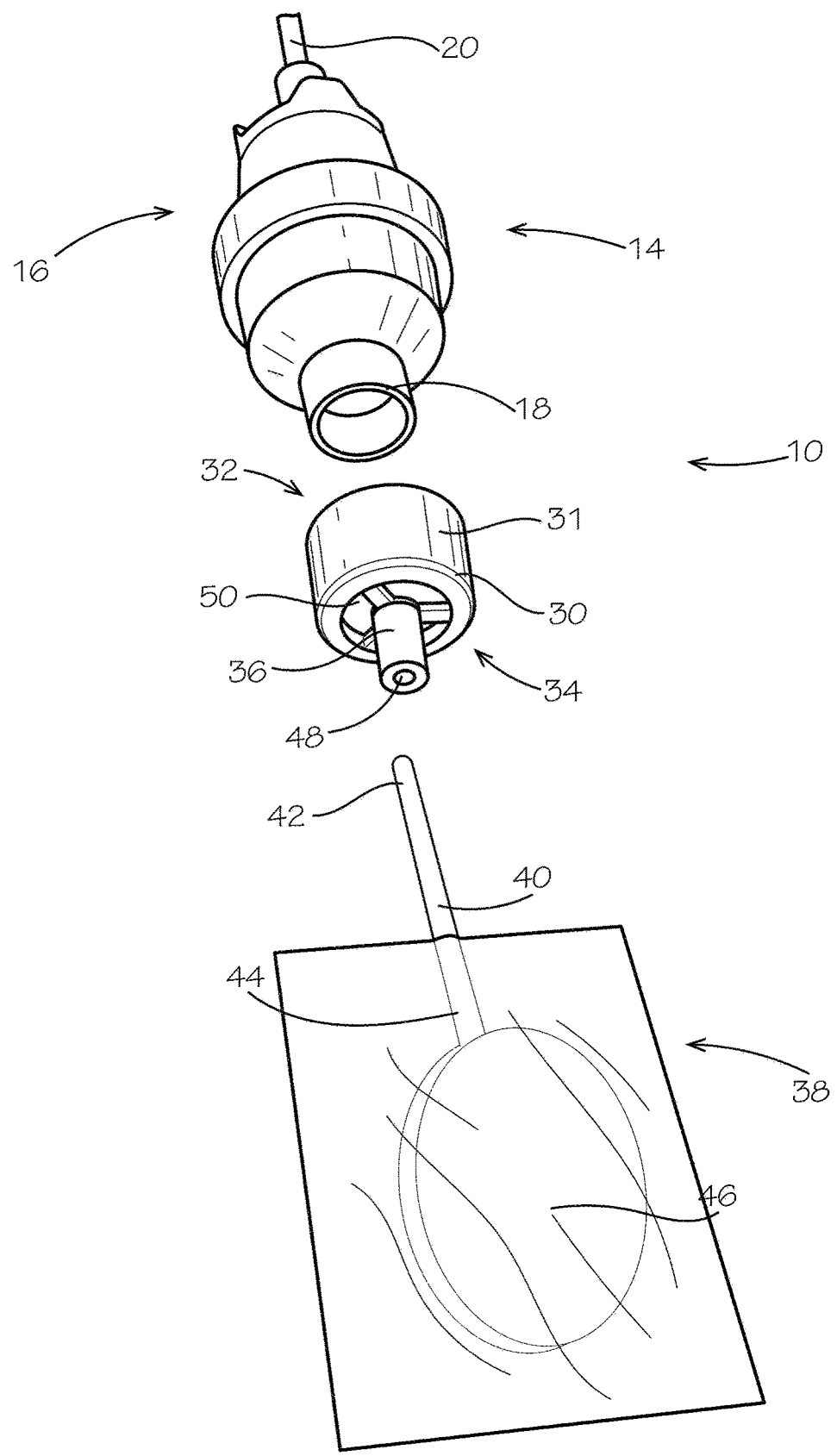
FIG. 7 is an exploded view of the device of FIG. 5.
Figure 8:
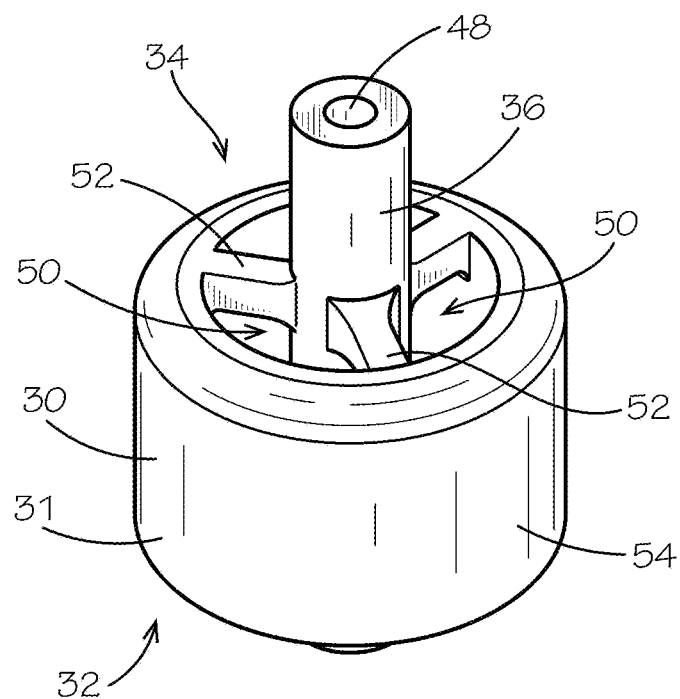
FIG. 8 is a top perspective view of a cap of the device of FIG. 5.
Figure 9:
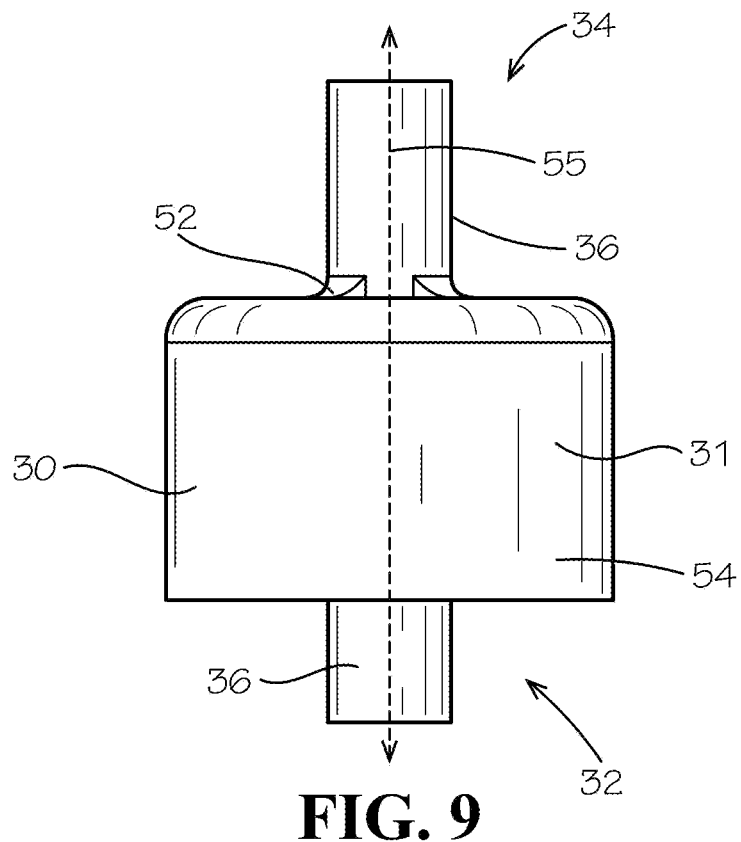
FIG. 9 is a front view of the cap of FIG. 8.
Figure 10:
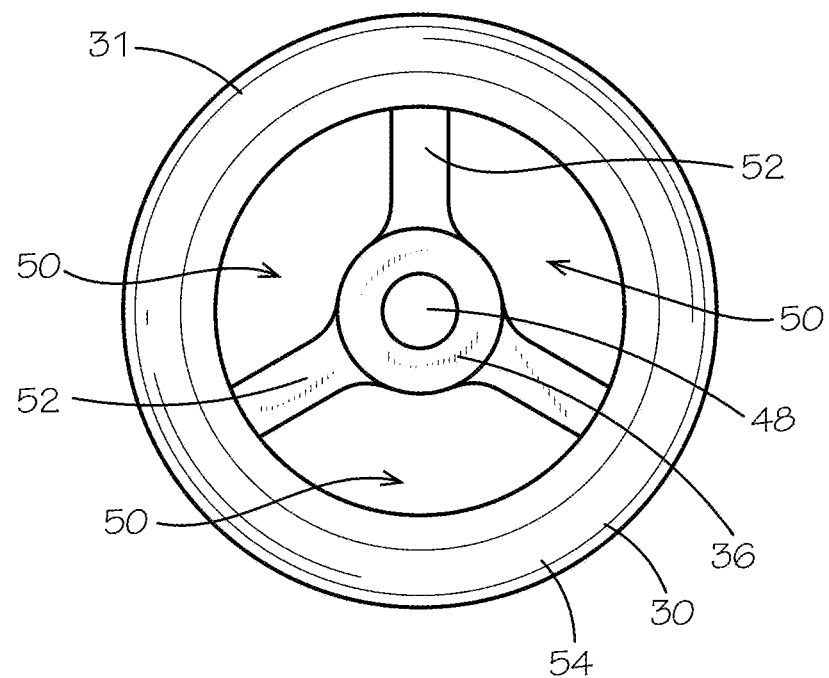
FIG. 10 is a top view of the cap of FIG. 8.
Figure 11:
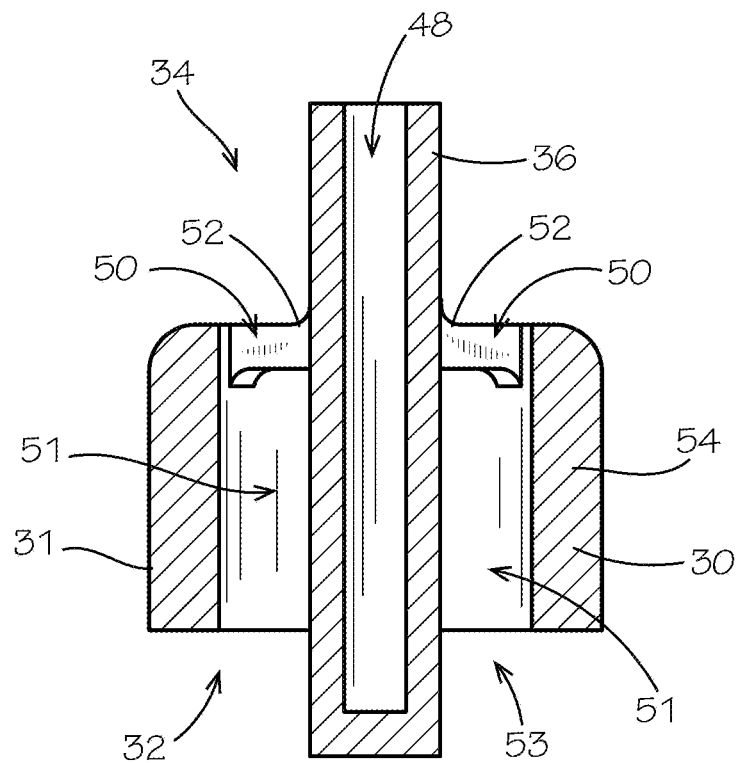
FIG. 11 is a cross-section view of the cap of FIG. 8.

A treat holder, edible item holder, or candy holder 36 can be disposed on the cap 30 and be accessible from the delivery side 34 of the cap 30. The candy holder 36 can be configured to receive or retain a candy or other edible item 38, the edible item 38 extending outward from the delivery side 34 of the cap 30. In some embodiments, the cap 30 can include a base 31, the candy holder 36 disposed on the base 31. In some embodiments, the candy holder 36 can extend outward from the base 31 toward the delivery side 34 of the cap 30. In other embodiments, the candy holder 36 can be positioned within the base 31 and can terminate at a delivery side of the base 31. In some embodiments, as shown in FIG. 7, the edible item 38 can be a sucker or lollipop type candy including a stick 40 having a proximal end 42 and a distal end 44. The proximal end 42 receivable in the candy holder 36, and a candy material 46 can be formed around the distal end 44 of the stick. In such embodiments, the candy holder 36 can include a candy holder recess 48 which can extend into the candy holder 36 from the delivery side 34 of the cap 30 toward the device side of the cap 30, or in other words be accessible from, oriented towards, or open to the delivery side 34 of the cap 30. The candy holder recess 48 configured to receive the stick 40 of the candy 38. In some embodiments, the candy holder recess 48 can be sized to create an interference or friction fit with the stick 40 of the candy 38 to retain the candy 38 in the candy holder 36.

In other embodiments, the candy holder 36 can be any suitable structure capable of receiving or being received in the edible item or candy 38. For instance in some embodiments, the candy holder 36 can be a protrusion which can extend outward from the delivery side 34 of the cap 30 and into a recess in the candy 38 to retain the candy 38 on the candy holder 36, such that the candy holder 36 effectively forms a stick for the candy 38. In some embodiments, the candy 38 can be integrally formed or molded onto the candy holder 36 of the cap 30, while in other embodiments, the candy 38 can be manufactured separately from the cap 30 and the candy holder 36, and the candy 38 can be installed on the candy holder 36 by a medical provider or by the patient themselves prior to treatment.

One or more apertures 50 can be defined in the delivery side 34 of the cap 30. The apertures 50 can fluidly communicate the breathing device side 32 of the cap 30 with the delivery side 34 of the cap 50, a pneumatic passage 51 can be formed between an opening 53 in the cap 30 and the one or more apertures 50, to allow passage of atomized medicine or oxygen from the supply device 14 out of the cap 30. In some embodiments, the apertures 50 can be defined in the base 31 of the cap 30. The apertures 50 can direct the atomized medicine or oxygen emitted by the breathing treatment delivery device 14 toward the patient's mouth or nose when the patient positions the edible item or candy 38 in the patient's mouth.

As such, a pass by breathing treatment can be delivered to the patient through the cap 30 while the patient enjoys the edible item or candy 38 positioned on the candy holder 36. The natural breathing of the patient while enjoying the candy 38 can cause the patient to breath in deeply to enhance the intake of the medicine or oxygen by the patient. In other embodiments, the patient can be instructed to follow a breathing protocol, for instance periodically taking deep breaths through the mouth or nose with the edible item 38 positioned in the patient's mouth.

As shown in FIGS. 8-11, in some embodiments, the cap 30 and the base 31 of the cap 30 can have a central axis 55, and the candy holder 36 can be positioned on and extend along the central axis 55. The apertures 50 can be spaced radially about the candy holder 36 on the delivery side 34 of the cap 30, such that apertures 50 are positioned around or encircle the candy holder 36. Such an orientation can allow medicine or oxygen from the breathing treatment delivery device 14 to be delivered proximate a patient's mouth or nose no matter what orientation the breathing treatment device 10 or the cap 30 is in when the candy 38 is positioned in the patient's mouth. In some embodiments, radial support arms 52 can extend from a sidewall 54 of the base 31 of the cap 30 to the candy holder 36, the radial arms 52 supporting the candy holder 36. The spaces between the radial arms 52 can form the apertures 50.

As shown in FIG. 9, in some embodiments, the candy holder 36 can extend below a lower end of the base 31 to accommodate a longer stick 44 of a candy or edible item 38, such that when the candy 38 is positioned in the patient's mouth the patient's mouth can still be located proximate the apertures 50 to help maximize intake of the oxygen or medication by the patient.

As shown in FIG. 11, in some embodiments, the base 31 can be a substantially hollow member which can receive a breathing treatment delivery device in an opening 53 in the device side 32 of the cap 30 and against an inner side of the side walls 54 of the base 31. The candy holder 36 can be positioned centrally on or within the base 31, with the candy holder recess 48 extending into the candy holder 36 and oriented toward or open to the delivery side 34 of the cap 30 such that the candy holder recess 48 is accessible from the delivery side 34 of the cap 30.

Figure 12:
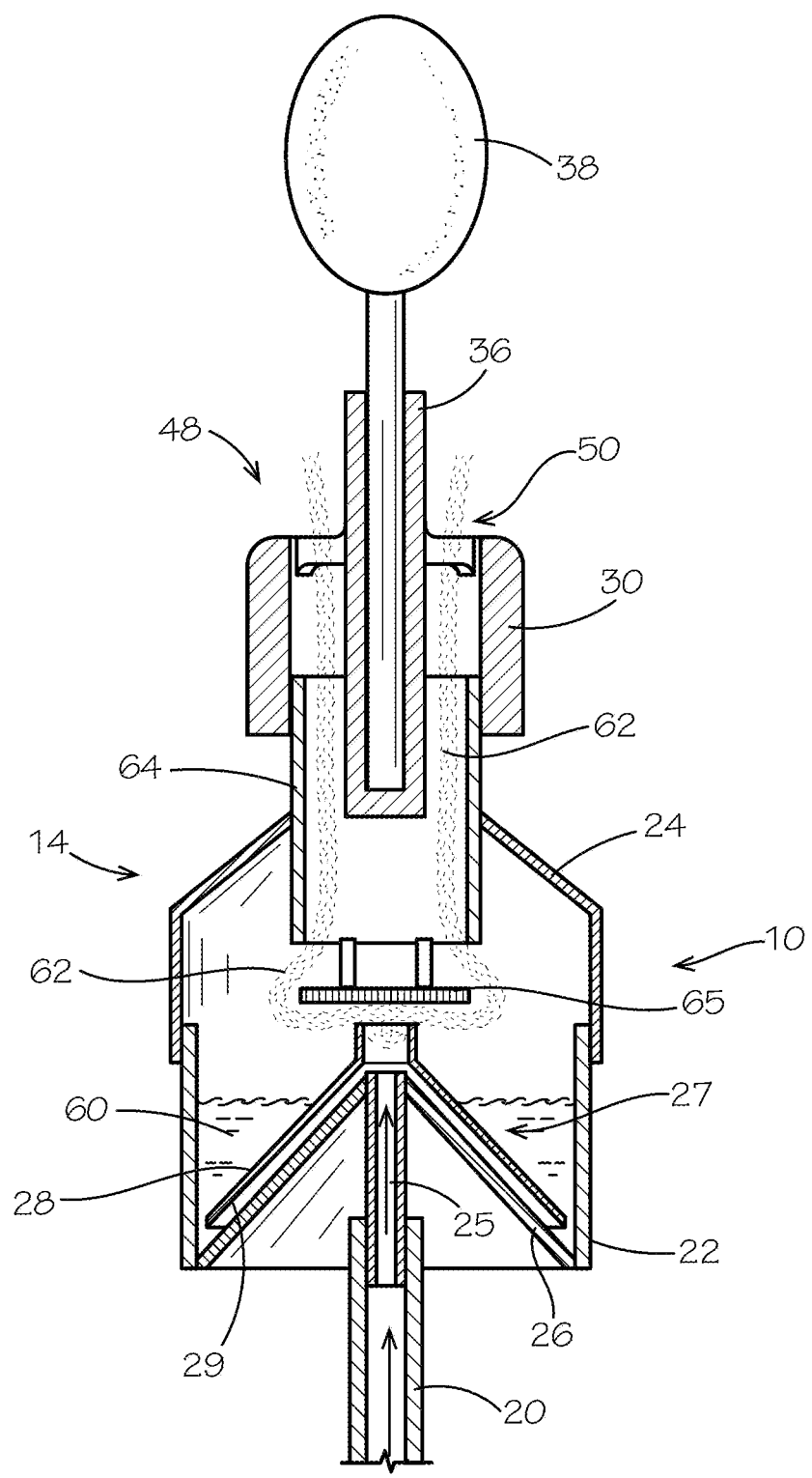
FIG. 12 is a cross-section view of the device of FIG. 5.
Figure 13:
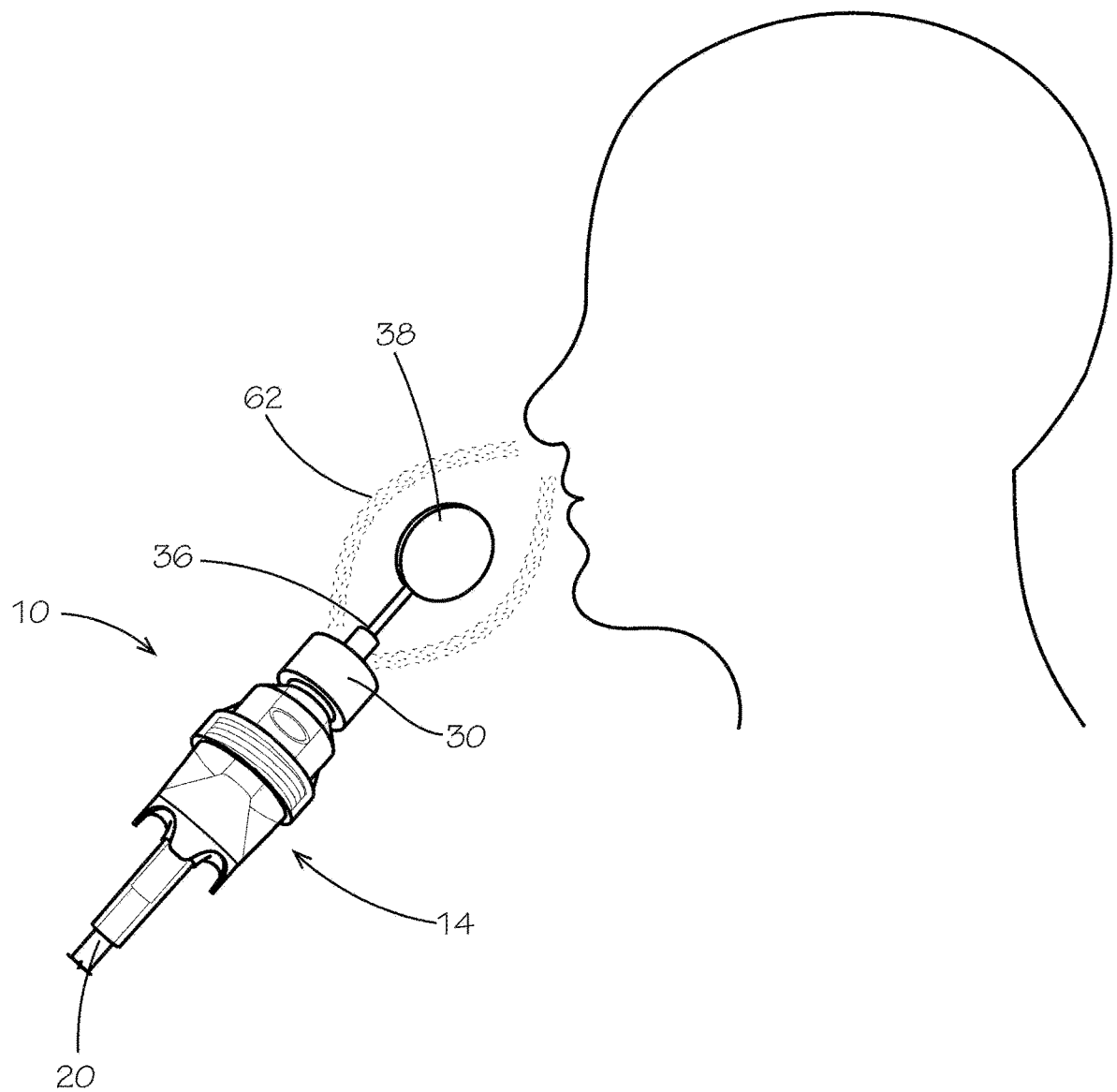
FIG. 13 is a perspective view of the device of FIG. 5 during use.
Figure 15:
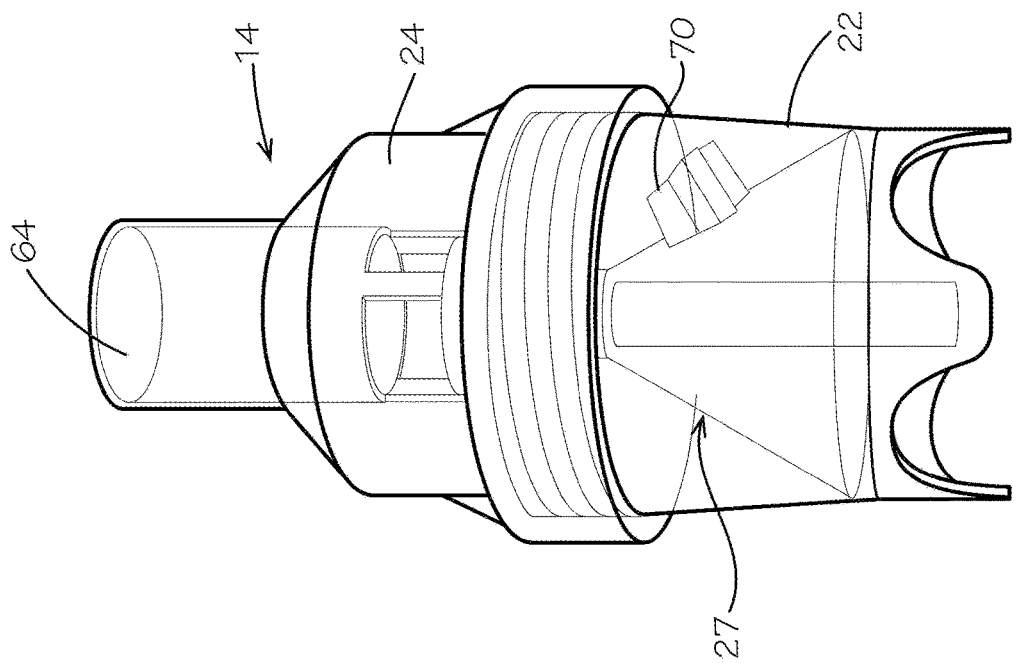
FIG. 15 is a front perspective view of a fully assembled nebulizer of the device of FIG. 14.
Figure 14:
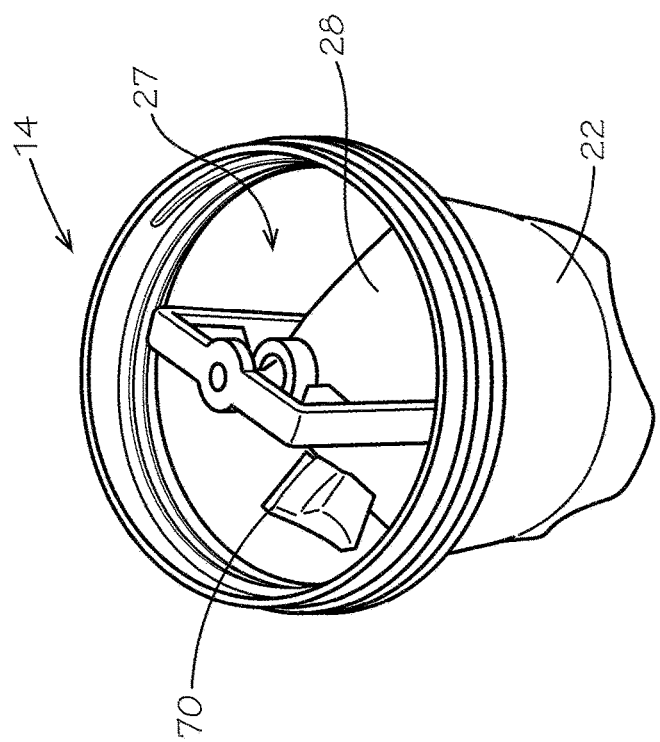
FIG. 14 is a perspective view of another embodiment of a breathing treatment delivery device including a flavor capsule in a medicine reservoir of the device.
Figure 16:
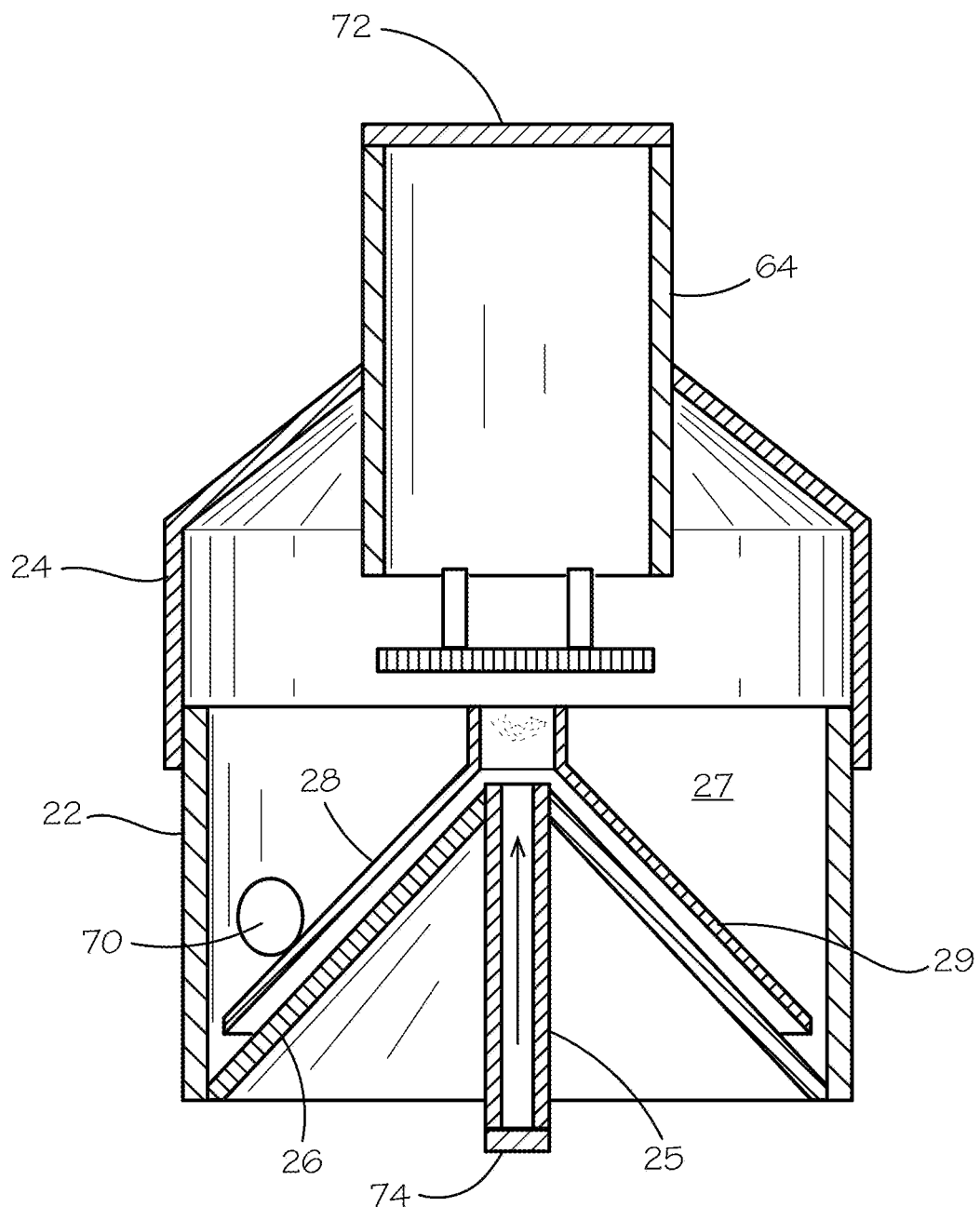
FIG. 16 is a cross-section view of the nebulizer of FIG. 15.

A detailed cross section view of a breathing treatment device 10 is shown in FIG. 12. A nebulizer device 14 is shown which can be used to atomize a liquid medicine into an atomized mist or spray. The nebulizer device 14 can include a pneumatic end 16 and a dispensing end 18. The pneumatic end 16 can be connected to a pneumatic line 20 such as an oxygen or other compressed gas line. Atomized medicine can be dispensed or emitted out of the dispensing end 18 of the nebulizer device 14.

The nebulizer device 14 in some embodiments can include a base portion 22 and a top portion 24. A lower floor 26 of the base portion 22 can have a tapered or frustrated conical shape in some embodiments. The base portion 22 can define a medicine reservoir 27 which can be configured to receive and hold liquid medicine. A pneumatic pathway 25 can extend up and through a center of the lower floor 26 of the base portion 22 and generally through the medicine reservoir 27. A cover member 28 can be positioned over the lower floor 26 of the base portion 22. The cover member 28 can have a tapered or frustrated conical shape that corresponds to the lower floor 26 of the base portion 22 and can be spaced from the lower floor 26 of the base portion 22 such that a medicine channel 29 is formed between the lower floor 26 of the base portion 22 and the cover member 28. The cover member 28 can include a central opening which aligns with the pneumatic pathway 25 such that the pneumatic pathway 25 can pass through the lower floor 26 of the base portion 22 and the cover member 28 when the cover member 28 is positioned over the lower floor 26. The opening in the cover member 28 and the pneumatic pathway 25 can define a path through the cover member 28 and the lower floor 26 of the base portion 22 for gases from the pneumatic line 20 to pass.

Liquid medicine 60 can be poured into the base portion 22 such that the medicine partially fills the base portion 22 and is contained below the opening in the cover member 28 and generally below the upper end of the pneumatic pathway 25 in the lower floor 26 of the base portion 22. The medicine channel 29 can be open to the pneumatic pathway 25 such that as gas flows from the pneumatic line 20 and through the pneumatic pathway 25, a negative pressure is produced within the channel which draws medicine 60 from within the medicine reservoir 27 up the medicine channel 29 toward the pneumatic passage 25. As the medicine 60 interacts with gas flowing through the pneumatic passage 25, the medicine 60 can become atomized and be emitted from the nebulizer as an atomized spray 62. In some embodiments, the nebulizer 14 can include a baffle 65 positioned above the pneumatic pathway 25 and generally between the pneumatic pathway 25 and the dispensing end 18 of the nebulizer. The baffle 65 can help liquid medicine further interact with pressurized gas or air passing through the pneumatic pathway 25 to continue atomizing any remaining liquid medicine in the atomized spray 62 or further atomize or reduce the size of medicine particles in the atomized spray 62.

The top portion 24 of the nebulizer device 14 can be positioned on and secured to the base portion 22 by way of an interference or a threaded interaction. The top portion 24 can have an exit channel 64 through which atomized spray 62 can be emitted from the nebulizer device 14. The cap 30 can be positioned on and can receive the exit channel 64 such that atomized spray 62 exiting or emitted by the nebulizer device 14 can be routed through the cap 30. The atomized spray 62 can pass through the apertures 50 and around the candy holder 36 and candy 38 positioned therein. As shown in FIG. 13, when the candy 38 is positioned in or near the patient's mouth, the cap 30 can direct atomized spray 62 through the apertures toward the patient's nose and mouth for an effective blow by treatment.

In some embodiments, as shown in FIGS. 14-16, the nebulizer device 14 can include a flavor capsule 70 positioned within the nebulizer 14 between the base portion 22 and the top portion 24 of the nebulizer device 14. The flavor capsule 70 can be configured to remain in solid form prior to use, but dissolve into liquid medicine as the liquid medicine is introduced into the base portion 22 of the nebulizer device 14. The flavor capsule 70 can provide a flavor or aroma to the medicine which can provide a pleasant smell and/or taste as the atomized medicine is breathed in by the patient. The flavor capsule 70 can help reduce anxiety in the patient during the breathing treatment by providing a pleasant or soothing smell and taste to the atomized medicine.

The flavor capsules 70 can be formed in a variety of shapes, sizes, colors, and flavors. In some embodiments, the flavor capsules 70 can match the flavor of the treat, edible item or candy 38 placed in the cap 30 such that medicine can help supplement the flavor of the edible item.

In some embodiments, the flavor capsules 70 can be individually packaged and provided separately from the nebulizer device 14. A patient or physician can remove the flavor capsule 70 from the packaging and place the flavor capsule 70 within the nebulizer device 14 before or after the liquid medicine is introduced into the nebulizer device 14. In other embodiments, the nebulizer device 14 can be prepackaged with the flavor capsule 70. A manufacturer can place a flavor capsule 70 within the nebulizer device 14 with the base portion 22 and the top portion 24 of the nebulizer device 14 secured together. The flavor capsule 70 can be hermetically sealed within the nebulizer device 14 to help prevent the flavor capsule 70 from spoiling or deteriorating over time. In some embodiments, a first heat sealed film 72 can be positioned over the exit channel 64 in the top portion 24 of the nebulizer device 14, and a second heat sealed film 74 can be positioned over a lower end of the pneumatic passage 25 in the lower floor 26 of the base portion 22. As such, the nebulizer device 14 can be sealed at both ends by respective heat sealed films or other suitable sealed protective layers to hermitically seal the flavor capsule 70 within the nebulizer device 14. In some embodiments, a gasket can be positioned at the interface between the top portion 24 and the base portion 22 of the nebulizer device 14 such that as the top portion 24 is secured to the base portion 22, a seal can be formed between the top portion 24 and the base portion 22 of the nebulizer device 14 to provide additional sealing protection for the flavor capsule 70 within the nebulizer device 14.

During use, the first and second films 72 and 74 can be removed, a pneumatic line can be connected to the pneumatic pathway 25, and medicine can be poured into the base portion 22 of the nebulizer device 14 to dissolve the flavor capsule 70 prior to atomization of the medicine.

Although some embodiments of the present invention have been shown and described, various modifications and substitutions may be made thereto without departing from the spirit and scope of the invention. Accordingly, it is to be understood that the present invention has been described by way of illustration and not limitation.

Thus, although there have been described particular embodiments of the present invention of a new and useful BREATHING DEVICE FOR MEDICAL TREATMENT, it is not intended that such references be construed as limitations upon the scope of this invention.

What is claimed is:

1. A breathing treatment delivery device for providing atomized medicine or oxygen to a patient, the breathing treatment delivery device comprising:

a supply device including a dispensing end, the supply device configured to dispense the atomized medicine or the oxygen through the dispensing end;

a cap having a device side and a delivery side, the device side including an opening receiving and in fluid communication with the dispensing end of the supply device;

a treat holder positioned on the delivery side of the cap;

a candy removably retainable by the treat holder, the candy including:

a stick having a proximal end and a distal end, the proximal end receivable by the treat holder; and a piece of candy formed around the distal end of the stick; and a plurality of apertures defined in the delivery side of the cap adjacent the treat holder and radially spaced about the treat holder on opposing sides of the treat holder, pneumatic passages formed through the cap between the opening in the device side of the cap and each of the plurality of apertures.

2. The device of claim 1, wherein the treat holder includes a treat holder recess extending from the delivery side of the cap towards the device side of the cap.

3. The device of claim 2, wherein the treat holder recess in the treat holder and the stick of the candy are sized to form an interference fit when the proximal end of the stick is received in the treat holder recess in the treat holder.

4. The device of claim 1, wherein the candy comprises a sugar free edible substance.

5. The device of claim 1, wherein the cap has a central axis, and the treat holder extends along the central axis of the cap.

6. The device of claim 5, wherein the treat holder is disposed centrally within the plurality of apertures.

7. The device of claim 1, wherein the supply device is a nebulizer configured to convert liquid medicine into the atomized medicine which is emitted through the dispensing end.

8. A breathing treatment delivery device for converting liquid medicine to atomized medicine and providing the atomized medicine to a patient, the breathing treatment delivery device comprising:

a nebulizer including a pneumatic end, a dispensing end and a medicine reservoir positioned between the pneumatic end and the dispensing end, the medicine reservoir shaped to receive the liquid medicine, the nebulizer operable to atomize the liquid medicine to produce the atomized medicine and dispense the atomized medicine through the dispensing end of the nebulizer; and a cap disposed on the dispensing end of the nebulizer, the cap comprising:

a nebulizer side and a delivery side, the nebulizer side disposed on and in fluid communication with the dispensing end of the nebulizer;

a candy holder disposed on the cap, the candy holder including a candy recess extending into the candy holder in a direction from the delivery side of the cap toward the nebulizer side of the cap;

a candy positioned in the candy holder, the candy having a stick removably received in the candy holder and a piece of candy formed around a distal end of the stick;

a plurality of apertures defined in the delivery side of the cap and radially spaced about the candy holder on opposing sides of the candy holder, the plurality of apertures fluidly communicating the nebulizer side of the cap with the delivery side of the cap to emit the atomized medicine received from the nebulizer through the plurality of apertures.

9. The device of claim 8, further comprising a flavor capsule positioned within the medicine reservoir, the flavor capsule being dissolvable in the liquid medicine placed in the medicine reservoir.

10. The device of claim 8, wherein the nebulizer includes a pneumatic pathway extending through the medicine reservoir.

11. The device of claim 10, wherein the medicine reservoir further comprises:

a tapered lower floor;

a tapered cover member having a shape corresponding to a shape of the tapered lower floor, and a medicine channel formed between the tapered lower floor and the tapered cover member, wherein the pneumatic pathway extends through the tapered lower floor and the tapered cover member.

12. The device of claim 11, further comprising a baffle positioned between the pneumatic pathway and the dispensing end of the nebulizer.

13. The device of claim 8, wherein the device side of the cap is shaped to produce an interference fit with the dispensing end of the nebulizer.

* * * * *